United States Patent [19]
Peters

[11] Patent Number: 5,178,633
[45] Date of Patent: Jan. 12, 1993

[54] SUTURE RING FOR HEART VALVE PROSTHESIS

[75] Inventor: T. Scott Peters, Georgetown, Tex.

[73] Assignee: Carbon Implants Inc., Austin, Tex.

[21] Appl. No.: 871,346

[22] Filed: Apr. 21, 1992

[51] Int. Cl.[5] .............................................. A61F 2/24
[52] U.S. Cl. ........................................ 623/2; 606/153
[58] Field of Search ................. 623/2, 1; 606/153, 151

[56] References Cited

U.S. PATENT DOCUMENTS

| | | | |
|---|---|---|---|
| 3,996,623 | 12/1976 | Kaster | 623/2 |
| 4,535,483 | 8/1985 | Klawitter et al. | 623/2 |
| 4,666,442 | 5/1987 | Arru et al. | 623/2 |
| 5,035,709 | 7/1991 | Wieting et al. | 623/2 |

Primary Examiner—David J. Isabella
Assistant Examiner—Dinh X. Nguyen
Attorney, Agent, or Firm—Fitch, Even, Tabin & Flannery

[57] ABSTRACT

A suture ring is provided for supporting a heart valve prosthesis having a valve body with an outer circumferential surface and an annular groove formed in the surface, and includes: a stiffening ring, having first and second ends, mounted in surrounding relationship about the valve body at the annular groove of the valve body, the stiffening ring including a tapered outer surface section; a resilient ring positioned about the outer circumferential surface of the body proximate the first end of the stiffening ring; a fabric tube, having a mesh weave body and first and second ends, covering the stiffening ring and the resilient ring, and interposed between the resilient ring and the stiffening ring; a first fastener band frictionally engaging the fabric tube between the first fastener band and the outer circumferential surface of the valve body proximate to the first end of the stiffening ring; a second fastener band frictionally engaging the fabric tube between the outer circumferential surface of the valve body proximate to the second end of the stiffening ring; first attachment means for attaching the first end of the fabric tube to a first location along the mesh weave body; and second attachment means for attaching the second end of the fabric tube to a second location along the mesh weave body.

18 Claims, 2 Drawing Sheets

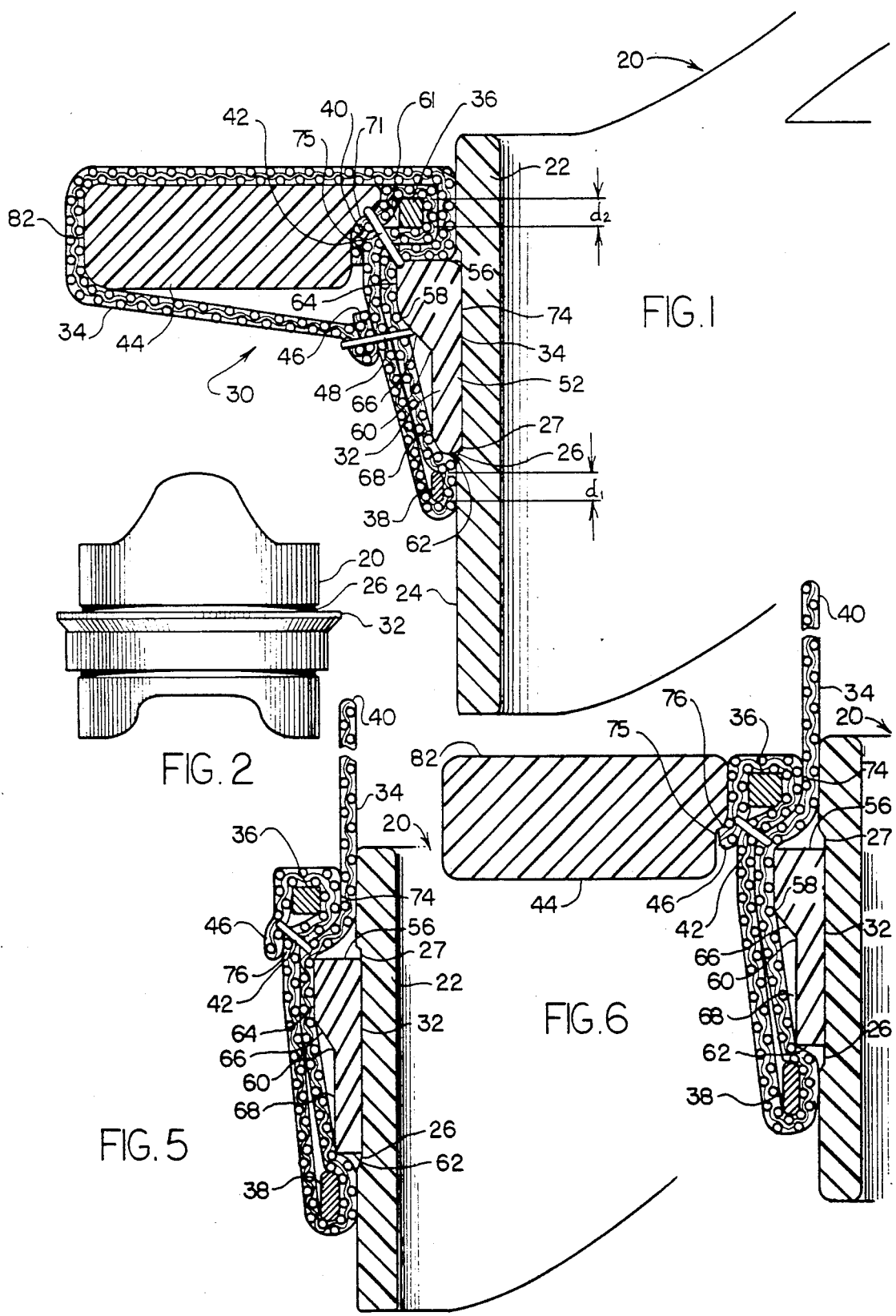

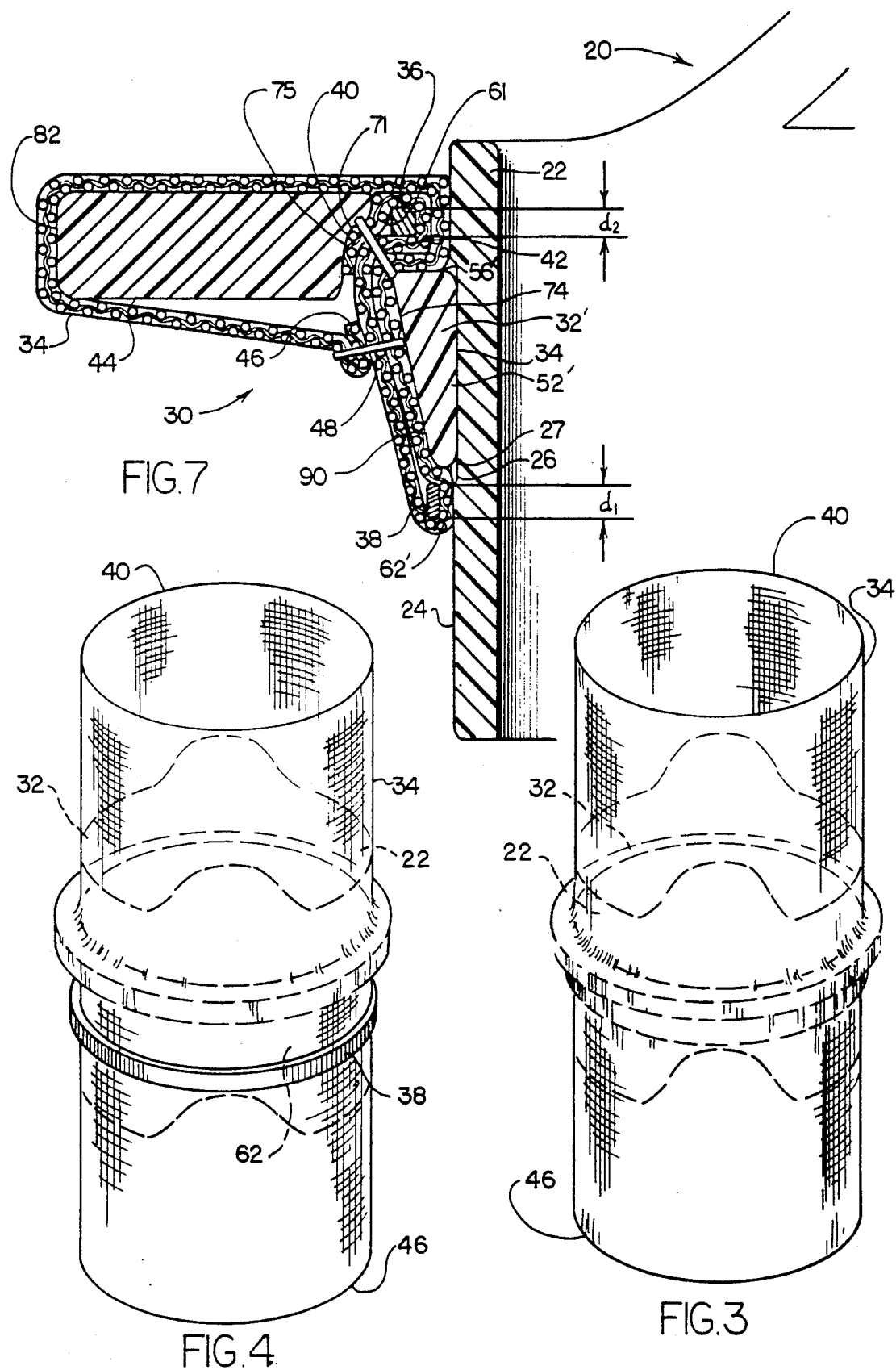

SUTURE RING FOR HEART VALVE PROSTHESIS

The present invention relates to heart valve prostheses, and more particularly, to suture rings for supporting heart valve prostheses.

BACKGROUND OF THE INVENTION

The use of artificial heart valves is well known in the art. The valves are typically supported in suture rings that are sewn to the surrounding tissues of the heart. Commonly used valves of the bileaflet type are disclosed in U.S. Pat. Nos. 4,254,508, 4,276,658, and 4,328,592. Such valves include two leaflets pivotally mounted within an orifice ring which is a conduit for blood. The leaflets pivot between an open position to allow blood to flow, and a closed position to prevent blood flow. The valve bodies, sometimes referred to as orifice rings, are typically formed of resilient materials, such as graphite, pyrocarbon, or pyrocarbon-coated graphite, and are typically designed to be deformed sufficiently to provide room to insert the leaflets, but which will return to an unstressed, annular configuration.

It is desirable to provide a structure for increasing the stiffness of the orifice ring after the leaflets are installed. Such structure is generally a stiffener ring mounted to the exterior of the orifice ring. The stiffener ring is held within a shallow annular groove formed in the outer circumferential surface of the orifice ring by an interference fit. The combination of the stiffener ring and the orifice ring provides greatly increased stiffness and resistance to deformation, compared to that of the orifice ring alone. Stiffener rings also provide an attachment site for affixing the suture ring to the valve. Another function of the stiffener ring is to provide a structure that resists forces that may be generated during implantation of the valve into the heart that could possibly damage the orifice ring, or damage or dislodge one of the leaflets.

U.S. Pat. No. 4,535,483 discloses a suture ring (hereinafter the '483 suture ring) which is designed to be mounted to a bileaflet valve of the type described above. The suture ring includes a stiffener ring which is seated and held within a groove formed in the outer circumferential surface of the orifice ring by an interference fit. The outer circumferential surface of the stiffener ring extends beyond the outer diameter of the orifice ring and provides an attachment site for the suture ring. The '483 suture ring includes a retainer ring having an inner annular groove and a ring of curved tines extending radially from one end of the retainer. The opposite side of the retainer ring has a ring of tangs with lugs extending radially inward towards the center of the ring. A resilient polymeric filler ring fits around the ring of tines and is held in place by a fabric material wrapped completely around the retainer ring, filler ring, and lugs. The fabric material, selected to be compatible with blood and heart tissue, is tied around the retainer ring with sutures. The assemblage of the retainer ring, filler ring, and fabric is mounted to the valve by pressing the retainer ring over the stiffener ring so that the lower surfaces of the lugs outwardly cam when they contact the upper edges of the stiffener ring. As the lugs cam outwardly, the tangs resiliently deform outwardly. When the flat upper surfaces of the lugs reach the bottom of the stiffener ring, the tangs spring back inwardly. At this stage, the stiffener ring is captured within the inner annular groove of the retainer ring whereby the retainer ring is secured to the orifice ring.

Although the '483 suture ring is an adequate design, if the retainer ring could be eliminated, there would be additional space for an orifice ring structure in the space normally occupied by the retainer ring so an orifice ring having a larger inside diameter could be used. Such an orifice ring could have a larger orifice flow area, and hence, relatively low fluid flow resistance. An orifice having low flow resistance would provide increased blood flow, a desirable characteristic in a mechanical heart valve.

U.S. Pat. No. 3,996,623, discloses a type of suture ring that is sewn to a heart valve with stitches. During implantation of a such a suture ring, the stitches holding the suture ring to the heart valve are vulnerable to inadvertently being cut by the surgeon, possibly causing the sewing ring to become separated from the heart valve. Therefore, there is a need for a suture ring that may be attached to a heart valve in a manner which is less susceptible to being damaged or cut.

There is also a need for a suture ring that does not require a retainer ring in order to accommodate an orifice ring having an overall larger orifice area than present orifice rings. A further need exists for a suture ring which supports a heart valve prosthesis where the valve may be rotated with relatively little torque to enable a surgeon to easily position the valve at the implantation site without risk of damaging the valve or the heart tissue.

SUMMARY OF THE INVENTION

A suture ring is provided for supporting a heart valve prosthesis in a heart of the type having a valve body with an outer circumferential surface and an annular groove formed in the surface. One advantage of the present invention is that it provides a suture ring that accommodates a heart valve prosthesis having a relatively large orifice flow area which supports increased blood flow. Another advantage is that a heart valve prosthesis supported by the suture ring may be rotated with very low torque to allow the valve to be more easily oriented at the implantation site. Yet another advantage of the suture ring of the present invention is that it requires fewer, more easily manufactured components than do prior art suture rings. Still another advantage of the suture ring is that it cannot be inadvertently separated from the heart valve during implantation.

Suture rings embodying various features of the present invention may include: a stiffening ring, having first and second ends, mounted in surrounding relationship about the valve body at the annular groove of the valve body, the stiffening ring including a tapered outer surface section; a resilient ring positioned about the outer circumferential surface of the body proximate the first end of the stiffening ring; a fabric tube, having a mesh weave body and first and second ends, covering the stiffening ring and the resilient ring, and interposed between the resilient ring and the stiffening ring; a first fastener band frictionally engaging the fabric tube between the first fastener band and the outer circumferential surface of the valve body proximate to the first end of the stiffening ring; a second fastener band frictionally engaging the fabric tube between the outer circumferential surface of the valve body proximate to the second end of the stiffening ring; first attachment means for attaching the first end of the fabric tube to a first location along the mesh weave body; and second attachment means for attaching the second end of the fabric tube to a second location along the mesh weave body.

The invention also includes the suture ring in combination with a heart valve.

BRIEF DESCRIPTION OF THE DRAWINGS

FIG. 1 is a cross-sectional view of an example of a heart valve prosthesis supported in a suture ring in accordance with the present invention.

FIG. 2 shows the assemblage of a stiffening ring mounted to the orifice ring in a first step of the assembly of the valve of FIG. 1.

FIG. 3 shows the fabric tube fitted over the assembly presented in FIG. 2.

FIG. 4 shows a first fastener band securing the fabric tube around the orifice ring.

FIG. 5 shows one end of the fabric pulled over the first fastener band and secured to the orifice ring with a second fastener band.

FIG. 6 shows the resilient ring fitted over the fabric tube and positioned around the fastener band.

FIG. 7 is a cross-sectional view of a second embodiment of a heart valve prosthesis supported in a suture ring in accordance with the present invention.

Throughout the specification and drawings, like components are referenced using like reference numerals.

DESCRIPTION OF THE PREFERRED EMBODIMENTS

The following description is of the best mode presently contemplated for practicing the invention. This description is not to be taken in a limiting sense, but is made for the purpose of describing the general principles of the invention. The scope of the invention should be determined with reference to the claims.

FIG. 1 illustrates a cross-sectional view of suture ring 30 supporting heart valve prothesis (hereinafter "heart valve") 20. Valve 20 may be a bileaflet valve of the general type disclosed in U.S. Pat. Nos. 4,254,508, 4,276,658, and 4,328,592, the disclosures of which are incorporated herein by reference. Heart valve 20 includes a valve body or orifice ring 22 having outer circumferential surface 24 in which shallow annular groove 26 is formed.

The following brief description presents a general overview of the present invention: Suture ring assembly 30 includes annular shaped metal stiffener ring 32 positioned within outwardly facing annular groove 26 of orifice ring 22 and held there by a slight interference fit. Fabric tube 34 covers stiffener ring 32 and is snugly held to outer circumferential surface 24 of orifice ring 22 by fastener bands 36 and 38 which are frictionally engaged around orifice ring 22. One end 40 of fabric tube 34 is folded around fastener band 36 and tied-off by suture 42. Resilient filler ring 44 is fitted over end 40 of fabric tube 34 and positioned proximate fastener band 36. Filler ring 44 is held in place by pulling or wrapping end 46 of fabric tube 34 around filler ring 44 and then sewing stitches or sutures 48 through end 46 and the two layers of fabric tube 34 near where the fabric tube overlies angled or needle guidance surface 66 of stiffener ring 32. Each of the components that comprise suture ring 30, as well as the assembly of suture ring 30, are discussed in greater detail further herein.

Stiffener ring 32 stiffens orifice ring 22 against deformation during surgical implantation of the assemblage of suture ring 30 and heart valve prosthesis 20. The inside circumferential surface 52 of stiffener ring 32 is preferably smooth and rectilinear to conform to the shape of outer circumferential surface 27 of groove 26. Stiffener ring 32 has a cross-sectional shape that is relatively wide from its upper end 56 (FIG. 1) to a first transition region 58, that is tapered, or wedge-shaped in a central section extending from the first transition region 58 to a second transition or junction 60 so as to provide a needle guidance surface 66, and that is relatively narrow and generally uniform along a lower cylindrical surface section 68 which extends to the lower end 62. The wide cross-sectional shape between the upper end 56 and the first transition region 58 of the stiffener ring 32 substantially improves the stiffness of the stiffener ring, and hence, the assembly of the stiffener ring and the orifice ring 22. The outer surface of stiffener ring 32 includes surface 64 between upper end 56 and first transition region 58, the tapered needle guidance surface 66 and cylindrical surface 68 between second transition region 60 and end 62.

Needle guidance surface 66 defines a frustum of a cone and has surprisingly been found to promote suturing of the valve to the heart tissue through the suture ring 30, as described in greater detail further herein, while protecting the orifice ring from possibly being damaged from impingement by a sewing needle as the surgeon stitches the suture ring 30 to the heart tissues. The wide end or base of the frustum is nearer, or proximal to resilient filler ring 44, whereas, the narrower end of the frustum is further, or distal, from the filler ring. To achieve the desired function of protecting the orifice ring, it has been found that the angle which the surface 66 forms with the cylindrical surface 68 should be between about 135° and about 150°.

The minimum thickness of stiffener ring 32 is greater than the depth of groove 26 so that the composite outer surface of stiffener ring 32 extends radially beyond outer surface 24 of orifice ring 22. The length of stiffener ring 32 is slightly less than the height of groove 26 to facilitate easy positioning of the stiffener ring within the groove. All of the edges of stiffener ring 32 are radiused to prevent abrasion of any material comprising fabric tube 34 that abuts stiffener ring 32.

Although in the final assembly, stiffener ring 32 is shielded by a fabric tube to prevent contact with blood or tissue, the material used to form the stiffener ring is selected for biocompatibility and thromboresistance. Further criteria for the stiffener ring material are that it preferably provide radiopacity and have a relatively high modulus of elasticity. In order to satisfy these requirements, stiffener ring 32 is preferably manufactured from a suitable chrome-cobalt alloy as well known in this art.

Fabric tube 34 is a biologically inert fibrous mesh weave structure or body that is interposed between the surrounding heart tissues and suture ring 30. Fabric tube 34 accommodates tissue ingrowth, or fibrosis between the tissues of the heart and the fibrous mesh weave body of the fabric tube. Fabric tube 34 covers stiffener ring 32 and is frictionally held against outer circumferential surface 24 of orifice ring 22 by first fastener band 36 positioned proximate to end 56 of stiffener ring 32, and by to the second fastener band 38 positioned proximate second end 62 of stiffener ring 32. End 46 of fabric tube 34 is pulled to wrap the fabric tube in a closed loop around outer circumferential surface 82 of resilient filler ring 44. End 46 then is sewn to fabric tube 34 proximate needle guidance surface 66 of stiffener ring 32 using suture 48. This loop of fabric tube 34 holds resilient polymeric filler ring 44 in position about orifice ring 22. One advantage of fastener bands 36 and 38 is that they securely hold fabric tube 34 around orifice ring 22 and cannot be inadvertently cut, which would deleteriously result in complete or partial separation of suture ring 30 from the orifice ring. Another advantage of the fastener bands is that they allow the orifice ring 22 to be easily rotated within the fabric tube 34 where the tube is interposed between the bands 36 and 38, and the orifice ring.

Fabric tube 34 may be formed of a woven or knitted fabric, such as Dacron or Teflon, selected for lifetime durability as well as compatibility with blood and heart tissue. The fabric tube that is employed may optionally be coated with vapor-deposited carbon, such as that sold under the mark Biolite, which gives the exposed fabric surface a highly thromboresistant surface.

Fasteners bands 36 and 38 generally have rectangular cross-sections and are preferably made of titanium, as for example, titanium 6AL-4V, because titanium rings may be easily fabricated by a number of manufacturing techniques such as boring, punching, or photoetching, and because titanium is biocompatible. Fastener bands 36 and 38 may also be manufactured from other metals including alloys of stainless steel, chrome, or cobalt. The depth, or thickness, $d_1$, of fastener band 36 in a direction transverse, or perpendicular to the outside diameter of the band, is preferably less than the depth, or thickness, $d_2$, of fastener band 36. The thickness, $d_2$, of the fastener band 38 is transverse to the direction of the outside diameter of the band 38. More particularly, $d_2$ is preferably about three times greater than $d_1$. The preference for the difference in the depths of the fastener bands 36 and 38 is attributable to the fact that at end 56 of stiffener ring 32, there are four material thicknesses of the mesh weave body of the fabric tube 34 in addition to the depth, $d_2$, of fastener band 36, whereas at end 62 of stiffener ring 32 there are two material thicknesses of mesh weave body of the fabric tube, in addition to the depth, $d_1$, of fastener band 38. In FIG. 7 it can be seen that there are two layers of the mesh weave body of the fabric tube between the fastener band 36 and the end 56 of the stiffener ring; and there is only one layer of the mesh weave body of the fabric tube between the end 62 and the fastener band 38. Therefore, the difference in the depths of the fastener bands 36 and 38 provides the benefit of positioning the suture ring generally centrally about the stiffening ring 32.

Filler ring 44 provides a support structure for facilitating attachment of suture ring 30 to the surrounding heart tissues because it is made of a resilient material easily penetrated by suturing needles through which stitches are sewn to attach suture ring 30 to the heart tissues. The material may be a pliable plastic in the uncured state which is compatible with human tissue and body fluids, as is well known in this art. Such plastic may be Dow Corning "Silastic", fluorosilicone rubber, or a similar synthetic resinous plastic material. This material cures at a relatively low temperature to a semirigid plastic which retains a molded shape, and is sterilizable, biologically inert, non-irritating, and non-toxic to body fluids and tissues.

Filler ring 44 has a generally rectangular cross-sectional area, except that gently curved inner circumferential surface 71 preferably includes a relatively shallow, concave groove 75 to accommodate the three material thicknesses of fabric tube 34 that are interposed between filler ring 44 and stiffener ring 32. Outer circumferential surface 82 of filler ring 44 is shaped to conform to the tissue wall surrounding the site where suture ring 30 is to be placed in the heart.

The assembly of suture ring 30 to heart valve 20 is initially described with reference to FIG. 2. Stiffener ring 32 is expanded by being heated to about 800° F. and then placed around the orifice ring in juxtaposition with groove 26 so that it cools to preferably provide an interference fit of about 0.0005-0.001 inch with the stiffener ring in the region of the groove. The orifice ring is preferably made from a graphite substrate coated with pyrocarbon. The relatively low stiffness of the orifice ring which allows it to be deflected to permit installation of the occluders is substantially enhanced when the orifice ring is mounted with an interference fit within the stiffening ring of the illustrated shape. The assembly of orifice ring 22 and stiffener ring 32 is inserted within fabric tube 34 as shown in FIG. 3. Referring to FIG. 4, fastener band 38 is placed over fabric tube 34 and positioned proximate end 62 of stiffener ring 44 so that fastener band 38 frictionally engages fabric tube 34 around orifice ring 22, securing it to the surface thereof.

Referring to FIG. 5, end 46 of fabric tube 34 is tightly pulled over fastener band 38 to form a double layer 74 of the material comprising fabric tube 34 (just beyond end 56) which envelops stiffener ring 32. Fastener band 36 then is placed over double layer 74 of the mesh weave body of the fabric 34 to frictionally and snugly engage fabric tube 34 and secure it between fastener band 34 and orifice ring 22. At this stage of assembly, stiffener ring 32 is completely covered by fabric tube 34. Next, the shorter end 46 of the fabric tube 34 is folded over fastener band 36, forming a triple layer 76 of the mesh weave body of the fabric tube as shown in FIGS. 1 and 5. End 46 is tied-off by sewing stitches, or sutures, 48 through end 46 and triple layer 76 completely around the outer circumference of orifice ring 22.

Referring to FIG. 6, the remaining longer end 40 of fabric tube 34 is inserted through resilient filler ring 44. Then, filler ring 44 is positioned about orifice ring 22 so that concave groove 75 abuts triple layer 76 of the mesh weave body of the fabric tube 34 proximate to fastener band 36. Returning to FIG. 1, end 46 of fabric tube 34 is pulled tightly around outer circumferential surface 82 of filler ring 44 and tied-off using stitches 48 sewn through four material thicknesses of fabric tube 34 around the outer circumference of stiffener ring 32 near needle guidance surface 66 of the stiffener ring. Needle guidance surface 66 also promotes quality control in the assembly of suture ring 30 because it tends to deflect any sewing needle (not shown) from inadvertently impinging and possibly damaging orifice ring 22.

One particular advantage of suture ring 30 is that the frictional engagement between the fabric tube 34 and the orifice ring 22 is controlled by the internal diameter of the fastener bands 36 and 38 and these diameters can be manufactured with precision. An important benefit of such precisely controlled inside diameters of the fastener bands is that the torque required for rotation of the valve within the fastener bands can be controlled within a narrow target range, e.g. about 3 in.-oz., so that the surgeon may easily rotate the orifice ring after the valve has been sutured in place at the implantation site.

The suture ring of the present invention may also be embodied to include a stiffener ring 32' having a tapered outer surface 90 which defines a frustum, as shown in FIG. 7. Stiffener ring 32' has a cross-sectional shape that is relatively wide at its upper end 56' near the fastener band 36 and tapers to a relatively narrow lower end 62' proximate the fastener band 38. The inside circumferential surface 52' of the stiffener ring 32' is preferably smooth and rectilinear to conform to the shape of outer circumferential surface 27 of groove 26. The stiffener ring 32' is expanded by being heated to about 800° F. and then placed around the orifice ring 22 in juxtaposition with groove 26 so that it cools to preferably provide an interference fit of about 0.0005–0.001 inch with the stiffener ring in the region of the groove. As with the tapered outer surface 66 of the stiffener ring 32, the tapered outer surface 90 likewise protects the orifice ring 22 from possibly being damaged from impingement by a sewing needle as the surgeon stitches the suture ring 30 to the heart tissues. The same procedures for assembling the suture ring 30 with the stiffening ring 32 are used to assemble the suture ring with the stiffening ring 32'.

The invention has been described in terms of a preferred embodiment; however, modifications obvious to one of ordinary skill in the art may be made without departing from the scope of the invention.

Particular features of the invention are emphasized in the claims which follow.

What is claimed is:

1. A suture ring for supporting a heart valve prosthesis having a valve body with an outer circumferential surface and an annular groove formed in said surface, the suture ring comprising:
    a stiffening ring, having first and second axial ends, mounted in surrounding relationship about said valve body at said annular groove of said valve body, said stiffening ring including a tapered outer surface section;
    a resilient ring positioned about the outer circumferential surface of said valve body proximate said first end of said stiffening ring;
    a fabric tube, having a mesh weave and first and second axial ends, covering said stiffening ring and said resilient ring, and interposed between said resilient ring and said stiffening ring;
    a first fastener band frictionally engaging said fabric tube between said first fastener band and said outer circumferential surface of said valve body proximate to said first end of said stiffening ring;
    a second fastener band frictionally engaging said fabric tube between said outer circumferential surface of said valve body proximate to said second end of said stiffening ring;
    first attachment means for attaching said first end of said fabric tube to a first location along said tube; and
    second attachment means for attaching said second end of said tube to a second location along said tube.

2. The suture ring of claim 1 wherein said tapered outer surface section defines a frustum having a wide first end and a narrow second end.

3. The suture ring of claim 2 wherein said wide first end of said frustum is nearer to said resilient ring than is said narrow second end of said frustum.

4. The suture ring of claim 3 wherein said stiffening ring is secured to said valve body by an interference fit.

5. The suture ring of claim 2 wherein said fabric tube is wrapped completely around said first and second fastener bands so as to totally envelop both said first and second fastener bands.

6. The suture ring of claim 5 wherein:
    said first fastener band has an outer diameter and a thickness, "$d_1$", transverse to said outer diameter; and
    said second fastener band has an outer diameter and a thickness, "$d_2$", transverse to said outer diameter, where $d_2 > d_1$.

7. The suture ring of claim 6 wherein $d_2 = 3d_1$.

8. The suture ring of claim 1 wherein said stiffener ring defines a frustum having a bore therethrough.

9. The suture ring of claim 1 wherein there are two layers of said tube interposed between said first end of said stiffener ring and said first fastener band and one layer of said tube interposed between said second end of said stiffener ring and said second fastener band.

10. In combination,
    a heart valve having an orifice ring providing a blood flow duct and having an annular groove about the outer circumferential surface of said orifice ring; and
    a suture ring comprising:
    a stiffening ring, having first and second axial ends, mounted in surrounding relationship about said valve body at said annular groove of said valve body, said stiffening ring including a tapered outer surface section;
    a resilient ring positioned about the outer circumferential surface of said valve body proximate said first end of said stiffening ring;
    a fabric tube, having a mesh weave and first and second axial ends, covering said stiffening ring and said resilient ring, and interposed between said resilient ring and said stiffening ring;
    a first fastener band frictionally engaging said fabric tube between said first fastener band and said outer circumferential surface of said valve body proximate to said first end of said stiffening ring;
    a second fastener band frictionally engaging said fabric tube between said outer circumferential surface of said valve body proximate to said second end of said stiffening ring;
    first attachment means for attaching said first end of said fabric tube to a first location along said tube; and
    second attachment means for attaching said second end of said tube to a second location along said tube.

11. The suture ring of claim 10 wherein said tapered outer surface section defines a frustum having a wide first end and a narrow second end.

12. The suture ring of claim 11 wherein said wide first end of said frustum is nearer to said resilient ring than is said narrow second end of said frustum.

13. The suture ring of claim 12 wherein said stiffening ring is secured to said valve body by an interference fit.

14. The suture ring of claim 11 wherein said fabric tube is wrapped completely around said first and second fastener bands so as to totally envelop both said first and second fastener bands.

15. The suture ring of claim 14 wherein:
    said first fastener band has an outer diameter and a thickness, "$d_1$", transverse to said outer diameter; and
    said second fastener band has an outer diameter and a thickness, "$d_2$", transverse to said outer diameter, where $d_2 > d_1$.

16. The suture ring of claim 15 wherein $d_2 = 3d_1$.

17. The suture ring of claim 10 wherein said stiffener ring defines a frustum having a bore therethrough.

18. The suture ring of claim 10 wherein there are two layers of said tube interposed between said first end of said stiffener ring and said first fastener band and one layer of said tube interposed between said second end of said stiffener ring and said second fastener band.

* * * * *

UNITED STATES PATENT AND TRADEMARK OFFICE
CERTIFICATE OF CORRECTION

PATENT NO. : 5,178,633
DATED : January 12, 1993
INVENTOR(S) : T. Scott Peters

It is certified that error appears in the above-indentified patent and that said Letters Patent is hereby corrected as shown below:

Column 2, line 15, delete "a" (first occurrence). Column 3, line 37, correct the spelling of "prosthesis"; line 53, change "40" to --46--; line 55, change "suture" to --a ring of sutures--; line 58, change "46" to --40--; line 59, change "46" to --40--. Column 4, line 56, after "ingrowth", delete the comma (,); line 62, delete "to the"; at the end of line 62, insert "to the"; line 66, change "46" to --40--. Column 5, line 25, change "36" to --38--; Column 6, line 29, change "34" to --36--; line 35, change "48" to --42--; line 55, after "38" insert a comma (,).

Signed and Sealed this

Fifteenth Day of March, 1994

Attest:

BRUCE LEHMAN

Attesting Officer

Commissioner of Patents and Trademarks